US009187764B2

(12) United States Patent
Hu et al.

(10) Patent No.: US 9,187,764 B2
(45) Date of Patent: Nov. 17, 2015

(54) CONTROLLABLE ON-OFF METHOD FOR FISH REPRODUCTION

(71) Applicant: Institute of Hydrobiology, Chinese Academy of Sciences, Wuhan, Hubei Province (CN)

(72) Inventors: Wei Hu, Wuhan (CN); Yunsheng Zhang, Wuhan (CN); Jun Dai, Wuhan (CN); Zuoyan Zhu, Wuhan (CN)

(73) Assignee: INSTITUTE OF HYDROBIOLOGY, CHINESE ACADEMY OF SCIENCES, Hubei Province (CN)

( * ) Notice: Subject to any disclaimer, the term of this patent is extended or adjusted under 35 U.S.C. 154(b) by 0 days.

(21) Appl. No.: 14/247,145

(22) Filed: Apr. 7, 2014

(65) Prior Publication Data

US 2014/0331346 A1    Nov. 6, 2014

(30) Foreign Application Priority Data

Feb. 7, 2013    (CN) .......................... 2013 1 0049161

(51) Int. Cl.
*C12N 15/85*    (2006.01)
*A01K 67/027*    (2006.01)

(52) U.S. Cl.
CPC ........ *C12N 15/8509* (2013.01); *A01K 67/0275* (2013.01); *A01K 2217/15* (2013.01); *A01K 2227/40* (2013.01); *A01K 2267/02* (2013.01)

(58) Field of Classification Search
CPC ........... A01K 2217/15; A01K 2227/40; A01K 2267/02; A01K 67/0275; C12N 15/8509
USPC .............................. 800/22; 435/375, 455, 458
See application file for complete search history.

(56) References Cited

U.S. PATENT DOCUMENTS

2005/0257281 A1*  11/2005  Hu et al. ........................ 800/20
2012/0144505 A1*   6/2012  Mumm et al. ..................... 800/3
2012/0304323 A1*  11/2012  Lauth et al. ..................... 800/21

FOREIGN PATENT DOCUMENTS

CN         102250932 A    11/2011

OTHER PUBLICATIONS

Weidinger et al. vol. 13, Issue 16, Aug. 19, 2003, pp. 1429-1434.*
Taiju Saito, et al., Xenogenesis in Teleost Fish Through Generation of Germ-Line Chimeras by Single Primordial Germ Cell Transplantation, Journal Article, Sep. 26, 2007, 159-166, Biology of Reproduction, Madison, Wisconsin.
Mary G. Goll, et al., Transcriptional Silencing and Reactivation in Transgenic Zebrafish, Journal Article, May 11, 2009, 747-755, Genetics Society of America, Bethesda, Maryland.
Ethan K. Scott, The Gal4/UAS toolbox in zebrafish: new approaches for defining behavioral circuits, Journal Article, Jul. 2009, 441-456, Journal of Neurochemistry.
Hu Wei, A perspective on fish gonad manipulation for biotechnical applications, Journal Article, Jan. 15, 2006, 1-7, vol. 51 No. 1, Chinese Science Bulletin 2006, Beijing, China.
Weidinger, Gilbert et al., "dead end, a Novel Vertebrate Germ Plasm Component, Is Required for Zebrafish Primordial Germ Cell Migration and Survival", Current Biology, Aug. 19, 2003, pp. 1429-1434, vol. 13, Elsevier Science Ltd.
Slanchev, Krasimir et al., "Development without germ cells: The role of the germ line in zebrafish sex differentiation", PNAS, Mar. 15, 2005, pp. 4074-4079, vol. 102, No. 11.
Heasman, Janet, "Morpholino Oligos: Making Sense of Antisense?" Developmental Biology, 2002, pp. 209-214, vol. 243, No. 2, Division of Developmental Biology, Cincinnati Ohio.
Wang, Yaping, "Genetic analysis of "all fish" growth hormone gene transferred carp (*Cyprinus carpio* L.) and its F1 generation", Chinese Science Bulletin, Jul. 2001, pp. 1175-1179, vol. 46, No. 14.
Nasevicius, Aidas et al., "Effective targeted gene 'knockdown' in zebrafish", Nature America Inc., Oct. 2000, pp. 216-220, vol. 26.

* cited by examiner

*Primary Examiner* — Janet Epps-Smith
(74) *Attorney, Agent, or Firm* — Maschoff Brennan (57) ABSTRACT

The invention discloses a method for controlling fish reproduction, the method comprises the following steps of: A, constructing a recombinant gene CMV-eGFP-SV40-CMV-Ga14-SV40 and establishing a GAL4 transgenic zebrafish line; B, constructing a recombinant gene CMV-RFP-SV40-UAS-antisense dnd and establishing a uas-antisensednd transgenic zebrafish line; and C, hybridizing by taking homozygous transgenic fish of the two lines as parents, and the hybrid generation fish was sterility. The method of the present invention takes a strategy that two fertilizable lines hybridized but hybrid generation is sterility, establishing a novel method with a universal meaning for controlling fish fertility; The method solves the contradiction of the reproductively sterility of fish and the hereditability of characters in a reproduction operation research and can be effectively applied to cultivation of new fish specie and population control.

1 Claim, 3 Drawing Sheets

CONTROLLABLE ON-OFF METHOD FOR FISH REPRODUCTION

FIELD OF THE INVENTION

The present invention relates to the technical field of genetic breeding of aquatic animals, and more particularly relates to a controllable on-off method for fish reproduction. The present invention adopts a strategy that two lines of fish parent are fertilized while the hybrid offspring induces sterility, and establishes a gal4 transgenic fish line and an antisense dnd transgenic fish line driven by UAS, respectively, the transgenic fish of the two lines are hybridized so that the reproductive development can be controlled in the hybrid offspring of fish, thereby establishing a manipulation technique for controlling fish reproduction, and new lines of fish having abortive gonads are bred.

BACKGROUND

Growth rate, meat quality and other traits are the main goals for improving fish varieties, and reproductive and developmental characteristics of fish have a very close relationship with these important traits. The Fish Energy Biology Research indicates that once the reproductive development of fish is controlled, their uptake of food will be more efficiently converted to the development of somatic cells, thus promotes growth. Many trout become poor in meat quality after the discharge of sex products when gonad maturation; while fish with less gonad development has higher content of essential amino acids, flavor amino acids in their muscle tissues. Therefore, the implementation of reproductive and developmental regulation of fish is an important guidance for cultivating new lines of cultured fish with excellent traits.

Since the advent of the first batch of transgenic fish (Zhu Z, Li G, He L, et al. Novel gene transfer into the fertilized eggs of goldfish (Carassius auratus L. 1758). Z angew Ichthyol, 1985, 1:31-34.), with the purpose of providing sources of high-quality food proteins, more than 30 kinds of transgenic fish have been successfully developed. Transgenic fish having been genetically modified has excellent traits as fast growth, high feed conversion efficiency, freeze and cold resistance, and strong disease resistance and the like. However, so far there is not a single case of industrial farming of transgenic fish, the bottleneck factor that restricts the industrialization of transgenic fish is the concern on its potential ecological risk. The potential ecological risk of transgenic fish is substantially closely related to its reproductive characteristics from a scientific view. The control of transgenic fish reproduction can fundamentally solve the potential ecological risk of transgenic fish (Hu Wei, Wang Yaping & Zhu Zuoyan. Progress in the evaluation of transgenic fish for possi-ble ecological risk and its containment strategies. Science in China Ser C-Life Sci. 2007, 50:573-579.).

GnRH antisense transgenic strategy is currently the preferred technique to control the reproduction of transgenic fish (Maclean N, Laight R J. Transgenic fish: an evaluation of benefits and risks. Fish and Fisheries, 2000, 1:146-172). The technique firstly represses the expression of GnRH gene which is related to fish gonadal development or sexual maturation by antisense transgene such that its gonadal development is inhibited, and reproduction of transgenic fish is controlled; on this basis, the technique restores the physiological fertility of unfertilized transgenic fish, and finally obtains fertility controllable transgenic fish without ecological risk.

However, even if a transgenic fish with complete infertile gonads is obtained by the use of said technique, it is in logical view an incomprehensible paradox how to transfer the "infertility" trait of the transgenic fish to the offspring and establish a line and is difficult to achieve in genetically view. Although it is theoretically possible to recover the physiological fertility of sterile transgenic fish through the artificial supply of exogenous hormones, it is found by relevant studies that the expression of GnRH gene of fish in the fish brain can start as early as the first day of fertilization and development, the laboratory to which the present inventors belonged has found that a supplement of exogenous GnRH gene at this stage will have an inhibition role in the embryonic development and the growth of juvenile fish, these restrictions make the success rate for fertility restoration very low. Moreover, even few sterile transgenic fish has its physiological fertility restored, the amount of sperms or eggs produced are very small, which is unable to meet the needs of large-scale production.

Gal4/UAS system has the potential to become an ideal inducible gene expression system used in the regulation of fish reproduction and development. Galactose regulated upstream promoter element Gal4 is a yeast transcriptional activator similar to the prokaryotic lactose operon, Gal4 protein has both DNA-binding domain and transcriptional activating domain. Upstream activat sequence UAS is another sequence in yeast that is similar to the enhancer sequence in higher eukaryotes. Gal4 activates the transcription of the downstream gene connected to UAS only when UAS is recognized, and has a strong specificity and controllability for the inducible expression of genes (Marnie E. Halpern, Jerry Rhee, Mary G. Goll, Courtney M. Akitake, Michael Parsons, and Steven D. Leach. Gal4/UAS Transgenic Tools and Their Application to Zebrafish. Zebrafish, 2008, 5 (2):97-110.).

Primordial germ cells are the precursor cells of germ cells, dead end (dnd) gene has an important role in the survival and migration of primordial germ cells (Gilbert Weidinger et al. dead end, a Novel Vertebrate Germ Plasm Component, Is Required for Zebrafish Primordial Germ Cell Migration and Survival, Current biology, 2003, (13):1429-1434.), the inhibition on the expression of dead end (dnd) gene can inhibit the normal migration of primordial germ cells, thereby inhibiting the formation and maturation of germ cells.

Zebrafish (Danio rerio) is currently a model fish that is widely used in the study of developmental biology, aquatic biotechnology and the like (Westerfield M. 1993. The Zebrafish Book: A Guide for the Laboratory Use of Zebrafish (Brachydanio rerio). University of Oregon Press, Eugene, Oreg.). It has guiding significance for the establishment of fish on-off reproduction technology, the breed of excellent farmed varieties of economic gonadal abortive fish and the control of exotic fish populations in the natural environment, etc. by taking zebrafish as a model to explore new methods for controlling fish reproduction.

SUMMARY OF THE INVENTION

A purpose of the present invention is to provide a method of controlling fish reproductive development. The method consists of two relatively independent but associated transgenic fish lines: one line is transformed with a strong CMV promoter-driven GAL4 expression vector, and the other line is transformed with a UAS sequence fused dnd antisense gene vector. The transgenic fish of these two lines can normally produce mature germ cells when exist separately, and can stably inherit traits to their offspring. However, once the two transgenic lines hybridized, in hybrid generation, GAL4 will induce UAS to drive the expression of downstream antisense dnd, thereby inhibiting the expression of the endogenous dnd gene. In light that dnd gene has an important role in the survival and migration of primordial germ cells, and therefore, the primordial germ cells in the hybrids can not migrate normally, eventually result it unable to form germ cells, thereby reproductively sterile fish is obtained.

The method of the present invention can become a new breeding technique for fish reproductive operation, and be used in cultivating new farmed fish lines with excellent traits, and can be applied to control exotic fish populations.

To achieve the above objects, the present invention adopts the following technical measures:

Construction of recombinant genes, comprising the following steps:

(1) Construction of recombinant gene CMV-eGFP-SV40-CMV-Gal4-SV40: 4× KGFP vector (Martin Distela et al. Optimized Gal4 genetics for permanent gene expression mapping in zebrafish. PNAS, 2009, 106:65-70.) was used as initial vector, and modified to obtain pSK-CMV-eGFP-SV40-CMV-MCS-SV40 vector (where CMV was cytomegalovirus gene promoter (589 bp, Clontech Inc. product); eGFP was Green fluorescent gene (Clontech Inc. product); SV40 was Simian vacuolating virus 40 poly A termination sequence (Clontech Inc. product); MCS was a multiple cloning site). By conventional methods (Molecular Cloning, Second Edition, J. SamBrooke et al., Science Press, 1993), Gal4 (Martin Distela et al. Optimized Gal4 genetics for permanent gene expression mapping in zebrafish. PNAS, 2009, 106:65-70.) was recombined to the downstream of CMV promoter, and constituted a Gal4 recombinant plasmid terminated by the poly A sequence of Simian vacuolating virus 40 (51 bp) (Clontech Inc. product); after digested with restriction endonuclease kpn I (TAKARA), a recombinant gene CMV-eGFP-SV40-CMV-Gal4-SV40, having a sequence shown in SEQ ID NO: 1 was obtained, wherein:

1-35: interval sequence; 36-624: CMV sequence; 625-647: interval sequence; 648-1472: eGFP sequence; 1473-1525: interval sequence; 1526-1576: SV40 sequence; 1577-1632: interval sequence; 1633-2221: CMV sequence; 2222-2250: interval sequence; 2251-2853: GAL4 sequence; 2854-2996: interval sequence; 2997-3047: Orange indicates SV40 sequence; 3048-3080: interval sequence.

(2) Construction of recombinant gene CMV-RFP-SV40-UAS-antisense dnd: the above constructed pSK-CMV-eGFP-SV40-CMV-MCS-SV40 vector was used as initial vector, and was modified to obtain pSK-CMV-RFP-SV40-UAS-antisense dnd transgenic vector, with main elements of (where CMV was cytomegalovirus promoter (Clontech Inc. product); RFP was red fluorescent gene (Clontech Inc. product); SV40 virus was Simian vacuolating virus 40 poly A termination sequence (Clontech Inc. product); 5× UAS was five copies of UAS sequence; MCS was multiple cloning site). Wherein 331 bp zebrafish dnd antisense gene (−74 bp-257 bp, dnd sequence from NCBI, NM_212795.1) was ligated in the direction of 3'-5' to the downstream of 5× UAS, and digested with restriction endonuclease kpn I (TAKARA), such that a recombinant gene CMV-RFP-SV40-UAS-antisense dnd, having the sequence shown in SEQ ID NO: 2 was obtained, wherein:

1-13: interval sequence; 14-602: CMV sequence; 603-610: interval sequence; 611-1288: RFP sequence; 1289-1443: interval sequence; 1444-1494: orange indicates SV40 sequence; 1495-1523: interval sequence; 1524-1640: 5× UASE1b sequence; 1641-1649: interval sequence; 1650-1980: antisense-dnd sequence; 1981-2129: interval sequence; 2130-2180: SV40 sequence; 2181-2213: interval sequence.

The method of controlling fish reproduction of the present invention, comprising the following steps:

(A) Introducing exogenous genes: Introducing recombinant genes CMV-eGFP-SV40-CMV-Gal4-SV40 and CMV-RFP-SV40-UAS-antisense dnd into fertilized eggs of zebrafish, respectively, by microinjection method (Zhu Z, Li G, He L, et al. Novel gene transfer into the fertilized eggs of goldfish (*Carassius auratus* L. 1758). Z angew Ichthyol, 1985, 1:31-34), to prepare P0 generation of GAL4 transgenic zebrafish and UAS-antisense dnd transgenic zebrafish.

(2) Transgenic fish lines: Screening P0 generation GAL4 transgenic zebrafish by the expression of green fluorescence protein gene observed by a fluorescence microscope (Olympus SZX12 type); and screening P0 generation UAS-antisense dnd transgenic zebrafish by the expression of red fluorescence protein gene observed by a fluorescence microscope (Olympus SZX12 type). Hybridizing the two P0 transgenic zebrafish with control zebrafish, respectively, to obtain F1 generation GAL4 transgenic zebrafish and UAS-antisense dnd transgenic zebrafish. Inbreeding the F1 generation GAL4 transgenic zebrafish, to obtain homozygous GAL4 transgenic zebrafish in F2 generation; and inbreeding the F1 generation UAS-antisense dnd transgenic zebrafish to obtain homozygous UAS-antisense dnd transgenic zebrafish in F2 generation.

(3) Using the homozygous GAL4 transgenic zebrafish and homozygous UAS-antisense dnd transgenic zebrafish as parents for hybridization of the transgenic fish of two lines, in the obtained hybrid generation, Gal4 will induce UAS to drive the expression of the antisense dnd downstream which significantly inhibits the level of dnd mRNA in the hybrid generation, leading a disorder of primordial germ cells migration in the hybrid offspring thus unable to complete the migration and eventually resulting in reproductive sterility of the hybrid fish offspring produced by the above mentioned lines.

The present invention has the following advantages over the prior art:

It is a traditional technique to control the fertility of transgenic fish by artificially inducing triploid fish using physical and chemical means, however, the efficiency of such artificially induced triploid is hard to reach 100% (Maclean and Laight Transgenic fish: an evaluation of benefits and risks. FISH and FISHERIES, 2000, 1:146-172.); another way is to cultivate sterile transgenic triploid fish using interploid cross of tetraploid fish and diploid fish, however, it is very difficult to cultivate tetraploid fish cable of self-reproduction and has genetic stability by intrasectional hybrid breeding, therefore, it is not universal to develop sterile transgenic triploid fish by interploid cross so as to solve the ecological safety issue of the transgenic fish (H U Wei et al. Progress in the evaluation of transgenic fish for possible ecological risk and its containment strategies. Chinese Sci Bull, 2007, 50:573-579).

GnRH gene antisense strategy is the preferred method that many laboratories are currently trying to establish which has a universal significance of controlling the sterility of transgenic fish. Meclean et al. obtained male steriled transgenic tilapia in the P0 generation of transgenic population through the GnRH gene antisense strategy (Maclean et al. Reversibly-sterile fish via transgenesis. ISB news report, 2003), the laboratory to which the present inventor belonged discovered transgenic carp having gonads abortion by inhibiting the expression of carp endogenous GnRHIII gene (Jing Xu et al. Defining Global Gene Expression Changes of the Hypothalamic-Pituitary-Gonadal Axis in Female sGnRH antisense Transgenic Common Carp (*Cyprinus carpio*). Plos one, 2011, 6 (6): e21057). In terms of cultivating new varieties of farmed fish, the "infertility" trait should be transferred to offspring to establish lines meanwhile inhibiting the reproductive development in fish.

However, when the expression of the endogenous GnRHIII gene was inhibited, it is very difficult to restore the physiological fertility of sterile transgenic fish by artificial supplement of exogenous GnRH gene. Moreover, even few sterile transgenic fish has its physiological fertility restored, the amount of sperms or eggs produced are very small, which is unable to meet the needs of large-scale production.

Some researchers controlled transgenic fish fertility by using Ntr/Met system, they firstly established a transgenic line having gonad-specifically expressed Ntr gene, then immersed the transgenic fish into Met during the breeding process, and converted metronidazole (Met) to cytotoxic by nitroreductase (Ntr), killed the germ cells of transgenic fish, so as to obtain the sterile transgenic fish (Chia-Chun et al. Inducible Male Infertility by Targeted Cell Ablation in Zebrafish Testis. Mar Biotechnol, 2010, 12: 466-478). Notably, this method required a long time for immersing the fish body in the drug Met, and the germ cells can be removed only after the production of cytotoxin was induced, therefore, it can not be applied to the breeding practices of transgenic fish aiming at providing food proteins.

As compared to the above-mentioned methods for controlling the reproduction of transgenic fish, the present invention applies a strategy that two fertilizable lines hybridized but hybrid generation is sterility, and cleverly solves the contradiction of the reproductively sterility and the hereditability of characters of fish. The present invention takes the dnd gene, which plays important role in the survival and migration of primordial germ cells, as a target gene, inhibits the expression of dnd gene in the hybrid offspring, such that the formation and maturity of the germ cells is inhibited from the source, which is a universal significant method for controlling fish reproduction. The present invention can cultivate new fish species having controllable fertility, and can be applied to control the population of foreign species, and is a new ecological safe technique for the manipulation of fish reproduction.

MODE TO CARRY OUT THE PRESENT INVENTION
Example 1

Recombinant Gene and Method for Constructing the Same (1) Construction of Recombinant Gene CMV-eGFP-SV40-CMV-Gal4-SV40 pEGFP-C1 (Clontech Inc. product) was double digested with DNA restriction endonuclease BglII and Xba I (TAKARA), under the condition of: 37° C. for 2 h, the digested product was purified by agarose gel electrophoresis (Axygen), and then the end was made blunt on PCR instrument (Veriti) using high-fidelity KOD PLUS enzyme (TAKARA), under the conditions of: 68° C. for 10 min, one cycle. The blunt product was ligated by T4 DNA ligase (NEB) at 4° C. overnight, and a PEGFP-C1 vector without multiple cloning site was obtained. Primers: CMV-eGFP-SV40-f/5'-GGAAGATCTTGGATAACCGTATTACCGCCAT-3' and CMV-eGFP-SV40-r/5'-CCGGATATCGTTTGGACAAACCACAACTAGAAT-3' (the underlined portion GGAAGATCT was the cleavage site for DNA restriction endonuclease BglII and its protection bases, CCGGATATC was the cleavage site for DNA restriction endonuclease EcoR V and its protection bases) were designed, the PEGFP-C1 vector having the multiple cloning site being removed were used as a template for PCR amplification by using high-fidelity KOD PLUS enzyme (TAKARA) on PCR instrument (Veriti) under the condition of: 95° C. 3 min, one cycle, 95° C. 30 s, 55° C. 30 s, 68° C. 2 min, 30 cycles, 68° C. 5 min, one cycle, the product was double digested with DNA restriction endonuclease BglII and EcoR V (TAKARA) under the conditions of: 37° C. for 2 h, the 4× KGFP vector (Martin Distela et al. Optimized Gal4 genetics for permanent gene expression mapping in zebrafish. PNAS, 2009, 106: 65-70.) was also double digested with DNA restriction endonuclease BglII and EcoR V (TAKARA) under the same conditions as above. The above digested fragments and backbone were ligated by T4 DNA ligase at 4° C. overnight to obtain pSK-CMV-eGFP-SV40 vector.

pEGFP-C1 (Invitrogen) was double digested with DNA restriction endonuclease AgeI and XhoI (TAKARA) under the condition of: water bath (Shanghai JingHong) at 37° C. for 2 h, the digested product was purified by agarose gel electrophoresis (Axygen), and then the end was made blunt on PCR instrument (Veriti) using high-fidelity KOD PLUS enzyme (TAKARA) under the conditions of: 68° C. for 10 min, one cycle. The blunt product was ligated by T4 DNA ligase (NEB) at 4° C. overnight, and a PEGFP-C1 vector without eGFP was obtained. Primers CMV-MCS-SV40-f/ 5'-CCGGATATCTGGATAACCGTATTACCGCCAT-3' and CMV-MCS-sV40-r/5'-ATAAGAATGCGGCCGC GTTTG-GACAAACCACAACTAGAAT-3' (the underlined portion CCGGATATC was the cleavage site for DNA restriction endonuclease EcoR V and its protection bases, ATAAGAATGCGGCCGC was the cleavage site for DNA restriction endonuclease NotI and its protection bases) was used, and the PEGFP-C1 vector having the eGFP being removed were used as a template for PCR amplification by using high-fidelity KOD PLUS enzyme (TAKARA) on PCR instrument (Veriti) under the condition of: 95° C. 3 min, one cycle, 95° C. 30 s, 55° C. 30 s, 68° C. 2 min, 30 cycles, 68° C. 5 min, one circle, the product was double digested with DNA restriction endonuclease NotI and EcoR V (TAKARA) under the conditions of: water Bath (Shanghai JingHong) at 37° C. for 2 h, pSK-CMV-eGFP-SV40 vector was also double digested with DNA restriction endonuclease NotI and EcoR V (TAKARA) under the same conditions as above. The above digested fragments and backbone were ligated by T4 DNA ligase at 4° C. overnight to obtain pSK-CMV-eGFP-SV40-CMV-MCS-SV40 vector (where CMV was cytomegalovirus promoter (589 bp, Clontech Inc. product); eGFP was green fluorescent gene (720 bp, Clontech Inc. product); SV40 virus was Simian vacuolating virus 40 poly A termination sequence (51 bp, Clontech Inc. product); MCS was multiple cloning site of 57 bp). The pSK-CMV-eGFP-SV40-CMV-MCS-SV40 vector was taken as a backbone to construct GAL4 transgenic vector. GAl4 gene was derived from vector TK5× C from (Martin Distela et al. Optimized Gal4 genetics for permanent gene expression mapping in zebrafish. PNAS, 2009, 106:65-70.).

Primers: GAL4-f/5'-CCCAAGCTTGCCGCCACCATGAAACTGCTC-3'; GAL4-r/5'-CGCGGATCCGAGGATGTCCAGGTCGTAGTC-3' (the underlined portion CCCAAGCTT was the cleavage site for DNA restriction endonuclease protection bases, CGCGGATCC was the cleavage site for DNA restriction endonuclease BamHI and its protection bases) were designed, and TK5×C vector were used as a template for PCR amplification by using high-fidelity KOD PLUS enzyme (TAKARA) on PCR instrument (Veriti) under the condition of: 95° C. 3 min, one cycle, 95° C. 30 s, 58° C. 30 s, 68° C. 1 min, 30 cycles, 68° C. 5 min, one cycle, and the product was double digested with DNA restriction endonuclease HindIII and BamHI (TAKARA) under the conditions of: water bath (Shanghai JingHong) at 37° C. for 2 h, pSK-CMV-eGFP-SV40-CMV-MCS-SV40 vector backbone was also double digested with DNA restriction endonuclease HindIII and BamHI (TAKARA) under the same conditions as above. The above digested fragments and backbone were ligated by T4 DNA ligase at 4° C. overnight to obtain GAL4 transgenic vector pSK-CMV-eGFP-SV40-CMV-Gal4-SV40, which was digested with DNA restriction endonuclease kpn I (TAKARA) to obtain GAL4 transgenic DNA fragment CMV-eGFP-SV40-CMV-Gal4-SV40, its nucleotide sequence is shown as SEQ ID NO: 1.

(2) Construction of recombinant gene CMV-RFP-SV40-UAS-antisense dnd

Information of single copy of UAS sequence and E1b sequence are from (Martin Distela et al. Optimized Gal 4genetics for permanent gene expression mapping in zebrafish. PNAS, 2009, 106: 65-70). Two single-stranded DNA which are partially complementary: NxUAS/f5'-CGGAGTACTGTCCTCCGAGCGGAGTACTGTC-3' and NxUAS/r5'-CTCGGAGGACAGTACTCCGCTCGGAGGACAG-3' (Synthesized by Invitrogen Company with 5' end phosphorylated) were designed, and PCR amplification was carried out using high-fidelity KOD PLUS enzyme (TAKARA) on PCR instrument (Veriti) under the condition of: 95° C. 30 s, 55° C. 30 s, 68° C. 10 s, 15 cycle, the PCR products were recovered by agarose gel electrophoresis, and was A-tailed by Taq polymerase (TaKARA), under the condition of: 72° C. 10 min, and then was ligated with PMD-18T (TAKARA) vector, sequenced (Invitrogen), and PMD-18T (TAKARA) vector containing 5 copies of UAS was screened.

Primers: 5xUAS-EcoR V/f5'-CCGGATATCCGGAGTACTGTCCTCCGAG-3' and 5xUAS-HindIII/r5'-CCCAAGCTTaaagtgaggctgagacgcgatgCTCGGAGGACAGTACTCCG-3' (the underlined portion CCGGATATC was the cleavage site for DNA restriction endonuclease EcoR V and its protection bases, CCCAAGCTT was the cleavage site for DNA restriction endonuclease HindIII and its protection bases, lowercase letters was E1b sequence), the PMD-18T (TAKARA) vector containing 5 copies of UAS was used as a template for PCR amplification by using high-fidelity KOD PLUS enzyme (TAKARA) on PCR instrument (Veriti) under the condition of: 95° C. 3 min, one cycle, 95° C. 30 s, 58° C. 30 s, 68° C. 30 s, 30 cycles, 68° C. 3 min, a circle, the product was purified by agarose gel electrophoresis (Axygen), and then was double digested with EcoR V and HindIII DNA restriction enzyme (TAKARA) under the condition of: water bath (Shanghai JingHong) at 37° C. for 2 h, and then the PCR product containing 5 copies of UAS was purified by agarose gel electrophoresis (Axygen) and recovered for use. The above constructed pSK-CMV-eGFP-SV40-CMV-MCS-SV40 vector was double digested with DNA restriction endonuclease EcoR V and HindIII (TAKARA) under the condition of: water bath (Shanghai JingHong) at 37° C. for 2 h, the digested products were purified by agarose gel electrophoresis (Axygen) and recovered for use.

Fragment containing five copies of UAS after digested with DNA restriction endonuclease HindIII and EcoR V and pSK-CMV-eGFP-SV40-CMV-MCS-SV40 vector backbone digested with DNA restriction endonuclease HindIII and EcoR V were ligated by T4 DNA ligase (NEB) at 4° C. overnight to obtain pSK-eGFP-5× UAS vector. The dnd mRNA sequence information of the dnd gene of zebrafish is from NCBI, NM_212795.1, and a region designed for antisense fragment is −74 bp-257 bp.

Total RNA was extracted from fertilized eggs in a cell stage with Trizol (ambion), digested using RNAase-free DNA enzyme (TOYOBO) for 30 min, and then cDNA was synthesized using reverse transcriptase (TOYOBO), the cDNA was used as a template, primers were:

Anti-dnd-Xba I/f5'-CTAGTCTAGAATGACCTTTTCTTGACTTTTCC-3' and Anti-dnd-HindIIIr5'-CCCAAGCTTGAGGCGAAACTCGTAAATGG-3' (the underlined portion CTAGTCTAGA was the cleavage site for DNA restriction endonuclease XbaI and its protection bases, CCCAAGCTT was the cleavage site for DNA restriction endonuclease HindIII and its protection bases), PCR amplification was conducted on PCR instrument (Veriti) with high-fidelity KOD PLUS enzyme (TAKARA), under the condition of: 95° C. 3 min, one cycle, 95° C. 30 s, 58° C. 30 s, 68° C. 1 min, 30 cycles, 68° C. 3 min, one cycle. The PCR products was purified by agarose gel electrophoresis (Axygen) and then double digested with DNA restriction endonuclease XbaI and HindIII (TAKARA) under the condition of: water bath (Shanghai JingHong) at 37° C. for 2 h, the PCR products after digestion was purified by agarose gel electrophoresis (Axygen) and then recovered for use.

The pSK-eGFP-5× UAS vector was double digested with DNA restriction endonuclease XbaI and HindIII (TAKARA) under the same conditions as above, and the digested PCR products were purified by agarose gel electrophoresis (Axygen) and then the purified pSK-eGFP-5× UAS backbone and the purified antisense dnd fragment were ligated by T4 DNA ligase (NEB) at 4° C. overnight, to obtain a pSK-eGFP-UAS-antisense dnd vector.

Primers: CMV-RFP-SV40-f/5'-GGAAGATCTGATCTATCAATTACGGGGTCAT-3' and MV-REP-SV40-f/5'-CCGGATATCCCCACAACTAGAATGCAGTGA-3' (GGAAGATCT was the cleavage site for DNA restriction endonuclease BgIII and its protection bases, CCGGATATC was the cleavage site for DNA restriction endonuclease EcoR V and its protection bases) were designed, pDsred2 (Invitrogen) vector was used as a template for PCR amplification on PCR instrument (Veriti) using high-fidelity KOD PLUS enzyme (TAKARA) under the condition of: 95° C. 3 min, one cycle, 95° C. 30 s, 55° C. 30 s, 68° C. 2 min, 30 cycles, 68° C. 3 min, one cycle, PCR product was purified by agarose gel electrophoresis (Axygen) and then double digested with DNA restriction endonuclease BgIII and EcoR V (TAKARA) under the condition of: water bath (Shanghai JingHong) at 37° C. for 2 h, the digested PCR product was purified by agarose gel electrophoresis (Axygen) and then recovered for use. Meanwhile, pSK-eGFP-UAS-antisense dnd vector was also double digested with DNA restriction endonuclease BglII and EcoR V (TAKARA) under the same conditions as above, the digested PCR product was purified by agarose gel electrophoresis (Axygen) and then recovered for use.

CMV-RFP-SV40 fragment after digested with DNA restriction endonuclease BglII and EcoR V and pSK-eGFP-UAS-antisense dnd backbone were ligated by T4 DNA ligase (NEB) at 4° C. overnight to obtain pSK-CMV-RFP-SV40-UAS-antisense dnd vector, which was digested with restriction endonuclease kpn I (TAKARA), to obtain the recombinant gene CMV-RFP-SV40-UAS-antisense dnd, having the sequence as shown in SEQ ID NO: 2.

In the above step (a) and step (2), the PCR reaction, digestion reaction, ligation reaction, DNA transformation, bacterial culture and the medium applied, etc., are all conventional manipulation for molecular biology and can be conducted according to "Molecular Cloning A Laboratory Manual", Second Edition, J. Sambrook et. al., Science Press, 1993.

Example 2

Cultivation of Homozygous Gal4 Transgenic Zebrafish and Homozygous UAS-Antisense dnd Transgenic Zebrafish, Comprising the Following Steps:

(A) Preparation of Transgenic Zebrafish

The fragments of recombinant genes CMV-eGFP-SV40-CMV-Gal4-SV40 and CMV-RFP-SV40-UAS-antisense dnd were dissolved in ST solution (88 mmol/l NaCl, 10 mmol/l Tris-HCl, pH 7.5), respectively, and adjusted to the final concentration of 85 ng/μl, the DNA solutions were introduced into animal pole of the fertilized eggs of zebrafish before the first cleavage using a microinjection method (Zhu Z, Li G, He L, et al. Novel gene transfer into the fertilized eggs of goldfish (Carassius auratus L. 1758). Z angew Ichthyol, 1985, 1:31-34), and dose of DNA is 1-2 nl/egg, the fertilized eggs were placed in a bath of 28.5° C. for incubation and farming after micromanipulation.

Figure 1:
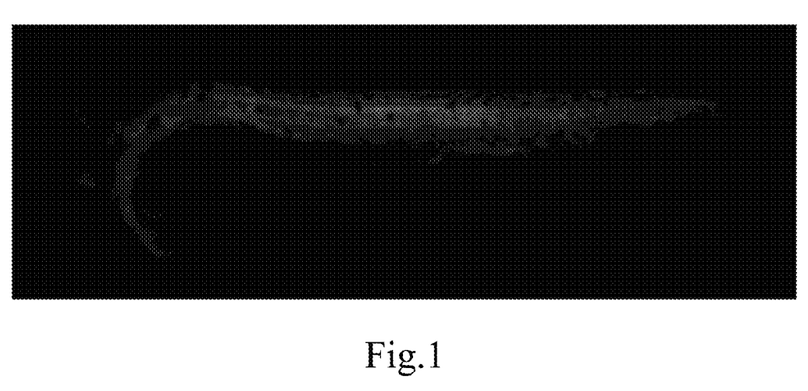
FIG. 1 is a schematic diagram showing a homozygous Gal4 gene transgenic zebrafish.

(2) Cultivation of Homozygous Gal4 Transgenic Zebrafish and Homozygous UAS-Antisense dnd Transgenic Zebrafish The fragment of recombinant gene CMV-eGFP-SV40-CMV-Gal4-SV40 was transformed to the fertilized eggs of zebrafish by micromanipulation, screened for the embryos expressing GFP by a fluorescence microscope (Olympus SZX12 type), which is the P0 generation of GAL4 transgenic zebrafish; the fragment of recombinant gene CMV-RFP-SV40-UAS-antisense dnd was transformed to the fertilized eggs of zebrafish by micromanipulation, screened for the embryos expressing red fluorescence by a fluorescence microscope (Olympus SZX12 type), which is P0 generation of UAS-antisense dnd transgenic zebrafish. The GAL4 transgenic zebrafish and UAS-antisense dnd transgenic zebrafish were cultured to sexual maturity in a recirculation aquaculture system, respectively, according to zebrafish manual (Westerfield M. (1993). The Zebrafish Book: A Guide for the Laboratory Use of Zebrafish (Zebrafish). University of Oregon Press, Eugene, Oreg.) and was hybridized with wild-type zebrafish, respectively, then screened for embryos that expressing eGFP and RFP (F1 generation) by a fluorescence microscope (Olympus Screening ZX12 type) and were cultured to sexual maturity; the sexual matured F1 generation of GAL4 transgenic zebrafish was inbred, and screened from the inbreeding population for the Individuals that express eGFP by a fluorescence microscope (Olympus SZX12 type) and cultured to sexual maturity, then test crossed with the control zebrafish, a test cross parent is the homozygous GAL4 transgenic zebrafish if the test cross progenies observed by fluorescence microscope all showed eGFP expression (FIG. 1).

Figure 2:
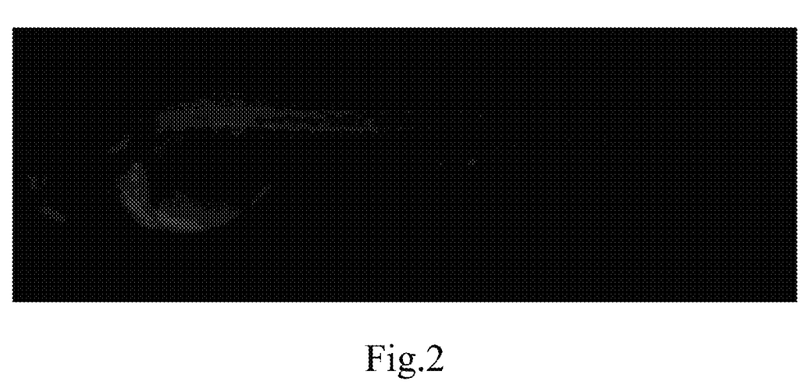
FIG. 2 is a schematic diagram showing a homozygous UAS-antisense dnd gene transgenic zebrafish.

Using the same method, the sexual matured F1 generation of UAS-antisense dnd transgenic zebrafish was inbred, screened from the inbreeding population for the Individuals that express RFP by a fluorescence microscope and cultured to sexual maturity, then test crossed with the control zebrafish, a test cross parent is the homozygous UAS-antisense dnd transgenic zebrafish if the test cross progenies observed by fluorescence microscope all showed RFP expression (FIG. 2).

The farming and reproduction of zebrafish, etc. are conducted according to the routine operation (Westerfield, 1993, The Zebrafish Book: A Guide for the Laboratory Use of Zebrafish (Zebrafish). University of Oregon Press, Eugene, Oreg.).

Example 3

A Method of Controlling Fish Reproduction

Figure 3:
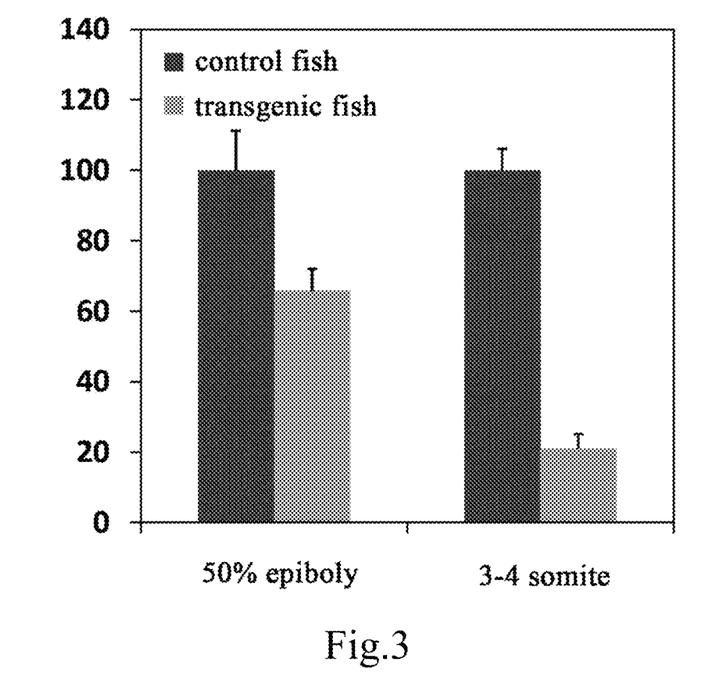
FIG. 3 is a schematic diagram showing the expression level of dnd gene in offspring of a control zebrafish and a two-line hybrid zebrafish.
Figure 4:
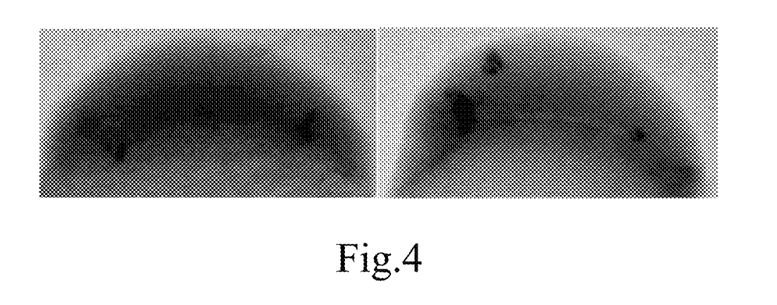
FIG. 4 is a schematic diagram showing the primordial germ cells migration of zebrafish, where a is the control zebrafish, and b is the two-line hybrid transgenic zebrafish.
Figure 5:
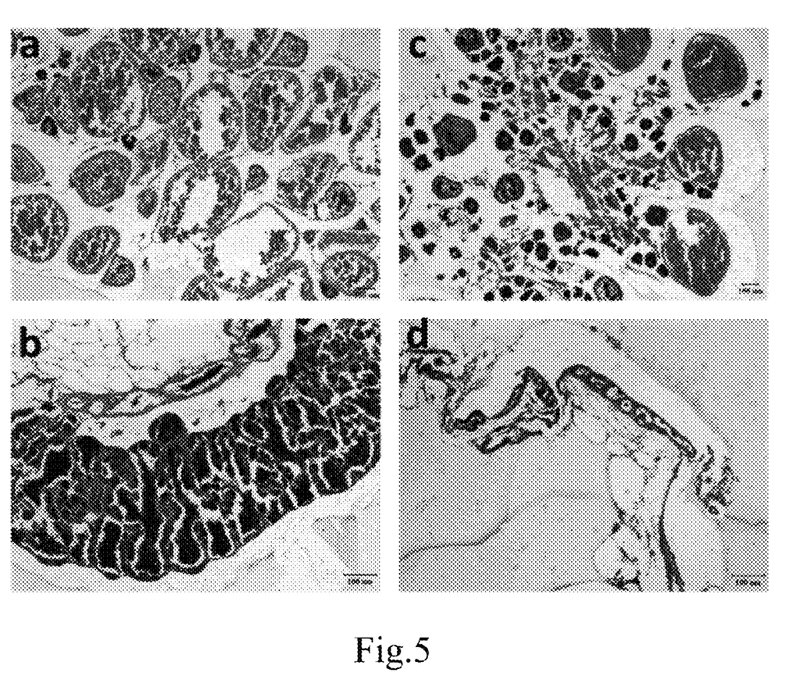
FIG. 5 is a schematic diagram showing a section of gonadal tissue of zebrafish, wherein a is the gonads tissue of a control female zebrafish, b is the gonads tissue of a control male zebrafish, c is the gonadal tissue of a two-line hybrid female zebrafish, and d is the gonadal tissue of a two-line hybrid male zebrafish.

The homozygous GAL4 transgenic zebrafish and homozygous UAS-antisense dnd transgenic zebrafish were used as parents, and hybridized according to conventional method to obtain hybrid experimental fish, in the experimental fish obtained by the hybridization of two lines of transgenic fish, Gal4 will induce UAS to drive the expression of the antisense dnd downstream, so that the expression level of the endogenous dnd mRNA in the hybrid experimental fish was significantly decreased (FIG. 3), leading a disorder of primordial germ cells migration in the hybrid offspring thus unable to complete the migration (FIG. 4) and eventually resulting in reproductive sterility of the hybrid fish offspring (FIG. 5). The expression of the endogenous dnd gene in the GAL4 transgenic zebrafish and UAS-antisense dnd transgenic zebrafish was determined by quantitative PCR method, the primordial germ cells migration characteristics was determined by embryo In-situ hybridization, and the status of gonadal development was test by biopsy.

Detection method for Dnd gene expression: Total RNA was extracted from the embryos of control zebrafish and the embryos of two-line hybrid transgenic zebrafish at 50% epiboly and 3-4 somite stage using Trizol (ambion), the specific operation was: approximately 100 mg of the collected embryos or tissue samples were homogenized in 1 ml Trizol, centrifuged at 12000 rpm, 4° C. for 10 min, the supernatant was transferred to another RNAase-free Ep tube, placed at room temperature for 5 min, was added by 200 μl chloroform and sharply shaken for 15 s then placed at room temperature for 5 min, then centrifuged at 12000 rpm, 4° C. for 15 min, the supernatant liquid was extracted to another RNAase-free Ep tube, added by 500 μl isopropyl alcohol and gently reversely mixed, placed at room temperature for 10 min, centrifuged at 12000 rpm, 4° C. for 10 min, the supernatant was discarded and added by 1 ml 75% (By volume) ethanol, mixed and shaken, centrifugal at 7500 rpm, 4° C. for 10 min, then the ethanol was discarded, and added by 30 μl RNAase-free water after dried for 15 min, thus the total RNA was obtained. 1 μg of total RNA was digested by RNAase-free DNA enzyme (TOYOBO) for 30 min and then reverse transcribed to cDNA (TOYOBO). 1 μl of 4 time-diluted cDNA was added as a template for each qPCR reaction, β-actin gene was used as an internal control, upstream primer: RT-β-actin-F sequence: 5'-ATGGCTTCTCTGCTCTGTATGGC-3', reverse primer: RT-β-actin-R sequence 5'-GAGGAGGGCAAAGTGGTAAAC-3'; dnd upstream primers RT-dnd-F: 5'-AAAAAAGGTGAC-CAAGGCAGT-3', downstream primer RT-dnd-R:

5'-CAAAAGAAAAGCGTGAAAACAT-3'. Formulated with 2× SYBR green realtime PCR mix (TOYOBO) to 20 μl system, reacted in real-time quantitative PCR instrument (BIO-RAD) under the condition of: 95° C. 2 min, one cycle, 94° C. 15 s, 58° C. 15 s, 72° C. 40 s, 40 cycles. The results showed that: the dnd mRNA levels of the embryos of the two-line hybrid transgenic zebrafish at 50% epiboly and 3-4 somite stages were approximately 65.8% and 20% that of the control, respectively (FIG. 3), T-test analysis (originPro6.1) showed that: the dnd mRNA levels were significantly decreased at both 50% epiboly and 3-4 somite stages compared to control (p<0.01).

Detection method for primordial germ cells migration: the GAL4 transgenic line and the UAS-antisense dnd transgenic line were hybridized, and the two-line hybrid embryos and the control zebrafish embryos were collected to 4% PFA-PBS (4 g PFA added to 100 ml PBS) 4.3 hours after fertilization and overnight at 4° C., the other day, immersed at 75% (by volume) PFA-PBS+25% (by volume) Methanol, 50% (by volume) PFA-PBS+50% (by volume) methanol and 25% (by volume) PFA-PBS+75% (Body Volume ratio) methanol, 100% methanol for 5 min, respectively, and the embryo in 100% methanol was stored at −20° C. until use. 900 bp (231-1130) of vasa (NM_131057) antisense probe was obtained from transcription by t7 RNA polymerase (Promega) and labeled by Digoxigenin (Roche), stored at −70° C. until use. All the subsequent operations were performed in full accordance with Thisse lab ISH 2010 update. Photos were taken by Digital camera (Nikon) on stereo microscopes (Olympus MVX10) after development.

The results showed that 72% of the embryos of two-line hybrid transgenic zebrafish appear phenomenon that PGCs was away from the yolk syncytial layer (YSL), and the appearance of this phenomenon in control embryos was just 11.1% (FIG. 4).

Gonadal tissue sections: the hybrid progeny of the GAL4 transgenic zebrafish and GAL4 UAS-antisense dnd transgenic zebrafish was cultured 5 months to full sexual maturity, the gonadal tissue of the hybrid offspring of the two-line transgenic zebrafish and the gonadal tissue of the control fish were taken and prepared paraffin sections.

The removed gonadal tissue was placed in 4% PFA-PBS (100 ml PBS added 4 g PFA) at 4° C., fixed overnight, then dehydrated, the specific operation was: the fixed tissue samples were placed in 70%, 80%, 85%, 90%, 95% (twice), 100% ethanol for 2 h, then placed in a mixture of ethanol and xylene (1:1 by volume) for 2 h, and then placed in xylene for 2 h, then allowed to stand for 2 h in a mixture of xylene and paraffin at 60° C. (volume ratio 1:1), and placed in paraffin at 60° C. for 2 h. Then paraffin embedded in paraffin-embedded instrument (KEDEE), and sliced into slices having thickness of 7 μm by paraffin slicer (KEDEE) after embedment, dried and stained with hematoxylin and eosin, the specific operational procedures was as follows: 100% ethanol (twice) 5 min, 95% ethanol (twice) 5 min, 85% ethanol, 3 min, 75% ethanol, 2 min, washed with distilled water for 1 min, stained with hematoxylin for 5 min, washed with distilled water for 2 min, differentiated by hydrochloric acid alcohol for 15 s, washed with water for 15 min, washed with distilled water for 2 min, 75% ethanol, 2 min, 85% ethanol, 2 min, stained with 0.5% eosin for 1 min, 95% ethanol (twice) 5 min, 100% ethanol (twice) 5 min, xylene (twice) 5 min. Sealed by neutral gum and then took photos with Digital camera (Nikon) on stereo microscopes (Olympus MVX10).

The results showed that about 60% of the eggs in the control female ovary were at the stage of the fourth development period which is to be matured, and about 20% of the eggs were at the third development stage, the rest 20% or so were at the first, second development period, while in the two-line hybrid female ovary, only about 3% were at the stage of the fourth development period, about 7% of the eggs were at the third development stage, and the rest 90% or so were at the first, second development period, and the arrangement of the eggs were very loose.

The lobular cavities in the control male testis was tightly ordered, and the entire cavity was filled with mature sperm, a lot of sperm cells about to maturity were located around the lobular cavities, while the two-line hybrid male testis is about one-tenth the size and number of the control, and arranged as a single row, 50% of the lobular cavities have almost no sperm, the rest lobular cavities has also relative low amount of sperms to the control (FIG. 5).

What is claimed is:

1. A method of controlling zebrafish reproduction, comprising the following steps:
   (A) Introducing exogenous genes: introducing recombinant genes CMV-eGFP-SV40-CMV-Gal4-SV40 and CMV-RFP-SV40-UAS-antisense dnd into fertilized eggs of zebrafish by microinjection method to prepare P0 generation of GAL4 transgenic zebrafish and UAS-antisense dnd transgenic zebrafish;
   The recombinant gene CMV-eGFP-SV40-CMV-Gal4-SV40 has a sequence shown in SEQ ID NO: 1;
   The recombinant gene CMV-RFP-SV40-UAS-antisense dnd has a sequence shown in SEQ ID NO: 2;
   (2) Obtaining homozygous transgenic zebrafish: zebrafish that expressing green fluorescent protein is P0 generation GAL4 transgenic zebrafish; and zebrafish that expressing red fluorescent protein is P0 generation UAS-antisense dnd transgenic zebrafish; hybridizing the two P0 transgenic zebrafish with control zebrafish, respectively, to obtain F1 generation GAL4 transgenic zebrafish and UAS-antisense dnd transgenic zebrafish; inbreeding the F1 generation GAL4 transgenic zebrafish, to obtain homozygous GAL4 transgenic zebrafish in F2 generation; and inbreeding the F1 generation UAS-antisense dnd transgenic zebrafish to obtain homozygous UAS-antisense dnd transgenic zebrafish in F2 generation;
   (3) Hybridizing transgenic zebrafish: hybridizing, by taking the homozygous GAL4 transgenic zebrafish and homozygous UAS-antisense dnd transgenic zebrafish as parents, the transgenic zebrafish of two lines, to produce sterilized zebrafish offspring.

* * * * *

SEQUENCE LISTING

<160> NUMBER OF SEQ ID NOS: 2

<210> SEQ ID NO 1
<211> LENGTH: 3080
<212> TYPE: DNA
<213> ORGANISM: Artifical
<220> FEATURE:
<223> OTHER INFORMATION: Synthesized

<400> SEQUENCE: 1

```
attagatctt ggataaccgt attaccgcca tgcattagtt attaatagta atcaattacg      60
gggtcattag ttcatagccc atatatggag ttccgcgtta cataacttac ggtaaatggc     120
ccgcctggct gaccgcccaa cgaccccgc ccattgacgt caataatgac gtatgttccc      180
atagtaacgc caatagggac tttccattga cgtcaatggg tggagtattt acggtaaact     240
gcccacttgg cagtacatca agtgtatcat atgccaagta cgcccctat tgacgtcaat      300 gacggtaaat ggcccgcctg gcattatgcc cagtacatga ccttatggga ctttcctact     360
tggcagtaca tctacgtatt agtcatcgct attaccatg tgatgcggtt ttggcagtac      420
atcaatgggc gtggatagcg gtttgactca cggggatttc caagtctcca ccccattgac     480
```

```
gtcaatggga gtttgttttg gcaccaaaat caacgggact ttccaaaatg tcgtaacaac      540
tccgccccat tgacgcaaat gggcggtagg cgtgtacggt gggaggtcta tataagcaga      600
gctggtttag tgaaccgtca gatccgctag cgctaccggt cgccaccatg gtgagcaagg      660
gcgaggagct gttcaccggg gtggtgccca tcctggtcga gctggacggc gacgtaaacg      720
gccacaagtt cagcgtgtcc ggcgagggcg agggcgatgc cacctacggc aagctgaccc      780
tgaagttcat ctgcaccacc ggcaagctgc ccgtgccctg gcccaccctc gtgaccaccc      840
tgacctacgg cgtgcagtgc ttcagccgct accccgacca catgaagcag cacgacttct      900
tcaagtccgc catgcccgaa ggctacgtcc aggagcgcac catcttcttc aaggacgacg      960
gcaactacaa gacccgcgcc gaggtgaagt tcgagggcga caccctggtg aaccgcatcg     1020
agctgaaggg catcgacttc aaggaggacg gcaacatcct ggggcacaag ctggagtaca     1080
actacaacag ccacaacgtc tatatcatgg ccgacaagca gaagaacggc atcaaggtga     1140
acttcaagat ccgccacaac atcgaggacg gcagcgtgca gctcgccgac cactaccagc     1200
agaacacccc catcggcgac ggccccgtgc tgctgcccga caaccactac ctgagcaccc     1260
agtccgccct gagcaaagac cccaacgaga gcgcgatca catggtcctg ctggagttcg     1320
tgaccgccgc cgggatcact ctcggcatgg acgagctgta caagtccgga ctcagatcct     1380
agataactga tcataatcag ccataccaca tttgtagagg ttttacttgc tttaaaaaac     1440
ctcccacacc tccccctgaa cctgaaacat aaaatgaatg caattgttgt tgttaacttg     1500
tttattgcag cttataatgg ttacaaataa agcaatagca tcacaaattt cacaaataaa     1560 gcatttttt cactgcattc tagttgtggt ttgtccaaac gatatctgga taaccgtatt     1620
accgccatgc attagttatt aatagtaatc aattacgggg tcattagttc atagcccata     1680
tatggagttc cgcgttacat aacttacggt aaatggcccg cctggctgac cgcccaacga     1740
cccccgccca ttgacgtcaa taatgacgta tgttcccata gtaacgccaa tagggacttt     1800
ccattgacgt caatgggtgg agtatttacg gtaaactgcc cacttggcag tacatcaagt     1860
gtatcatatg ccaagtacgc cccctattga cgtcaatgac ggtaaatggc ccgcctggca     1920
ttatgcccag tacatgacct tatgggactt tcctacttgg cagtacatct acgtattagt     1980
catcgctatt accatggtga tgcggttttg gcagtacatc aatgggcgtg gatagcggtt     2040
tgactcacgg ggatttccaa gtctccaccc cattgacgtc aatgggagtt tgttttggca     2100
ccaaaatcaa cgggactttc caaaatgtcg taacaactcc gccccattga cgcaaatggg     2160
cggtaggcgt gtacgtggg aggtctatat aagcagagct ggtttagtga accgtcagat     2220
ccgctagcgc taccggtcga gctcaagctt gccgccacca tgaaactgct ctcatccatc     2280
gagcaagcct gcgacatttg tcggcttaag aagctgaaat gctccaagga aaagccgaaa     2340
tgtgccaaat gcctgaagaa caattgggaa tgtcgttact ctcccaaaac caagcgaagt     2400
ccactcacaa gggctcatct gaccgaagtg gagagcaggc tagagagact ggaacaactc     2460
tttttgctca tcttccctag agaggacctt gacatgatcc tcaagatgga ttctctccag     2520
gatattaaag ccctttttgac tggcttattc gtccaggaca atgtgaacaa agacgctgtg     2580
acagaccgat tggcaagtgt cgagaccgat atgcctctga cactgagaca gcacagaatc     2640
agcgctactt cctcaagcga agagtcttct aacaagggac agagacagct gactgtttcg     2700
agcaggtcga ccccgtcccc ggccgacgcc ctggacgacg cgacctgga catgctgcct     2760 gctgatgctc tcgatgattt cgatctggat atgctcccgg ccgacgccct ggacgactac     2820
```

```
gacctggaca tcctccggat ccaccggatc tagataactg atcataatca gccataccac    2880
atttgtagag gttttacttg ctttaaaaaa cctcccacac ctcccctga acctgaaaca     2940 taaaatgaat gcaattgttg ttgttaactt gtttattgca gcttataatg gttacaaata    3000
aagcaatagc atcacaaatt tcacaaataa agcattttt tcactgcatt ctagttgtgg     3060
tttgtccaaa cgcggccgcc                                                3080

<210> SEQ ID NO 2
<211> LENGTH: 2213
<212> TYPE: DNA
<213> ORGANISM: Artifical
<220> FEATURE:
<223> OTHER INFORMATION: Synthesized

<400> SEQUENCE: 2
attagatctt acctagttat taatagtaat caattacggg gtcattagtt catagcccat      60
atatggagtt ccgcgttaca taacttacgg taaatggccc gcctggctga ccgcccaacg    120 accccgccc attgacgtca ataatgacgt atgttcccat agtaacgcca atagggactt     180
tccattgacg tcaatgggtg gagtatttac ggtaaactgc ccacttggca gtacatcaag    240
tgtatcatat gccaagtacg ccccctattg acgtcaatga cggtaaatgg cccgcctggc    300
attatgccca gtacatgacc ttatgggact ttcctacttg gcagtacatc tacgtattag    360
tcatcgctat taccatggtg atgcggtttt ggcagtacat caatgggcgt ggatagcggt    420
ttgactcacg gggatttcca agtctccacc ccattgacgt caatgggagt ttgttttggc    480
accaaaatca acgggacttt ccaaaatgtc gtaacaactc cgccccattg acgcaaatgg    540
gcggtaggcg tgtacggtgg gaggtctata taagcagagc tggtttagtg aaccgtcaga    600
tcgggatccg atggcctcct ccgaggacgt catcaaggag ttcatgcgct tcaaggtgcg    660
catggagggc tccgtgaacg gccacgagtt cgagatcgag ggcgagggcg agggccgccc    720 ctacgaggc acccagaccg ccaagctgaa ggtgaccaag gcggccccc tgcccttcgc     780 ctgggacatc ctgtcccctc agttccagta cggctccaag gcctacgtga agcaccccgc    840
cgacatcccc gactacttga agctgtcctt ccccgagggc ttcaagtggg agcgcgtgat    900
gaacttcgag gacggcggcg tggtgaccgt gacccaggac tcctccctgc aggacggcga    960
gttcatctac aaggtgaagc tgcgcggcac caacttcccc tccgacggcc ccgtaatgca   1020
gaagaagacc atgggctggg aggcctccac cgagcggatg taccccgagg acggcgccct   1080
gaagggcgag atcaagatga ggctgaagct gaaggacggc ggccactacg acgccgaggt   1140
caagaccacc tacatggcca gaagcccgt gcagctgccc ggcgcctaca agaccgacat    1200
caagctggac atcacctccc acaacgagga ctacaccatc gtggaacagt acgagcgcgc   1260
cgagggccgc cactccaccg gcgcctaaga attggccgcg actctagatc ataatcagcc   1320
ataccacatt tgtagaggtt ttacttgctt taaaaaacct cccacacctc ccctgaacc    1380 tgaaacataa aatgaatgca attgttgttg ttaacttgtt tattgcagct tataatggtt   1440
acaaataaag caatagcatc acaaatttca caaataaagc atttttttca ctgcattcta   1500
gttgtggtag ccgatatcc cggcggagta ctgtcctccg agcggagtac tgtcctccga    1560
gcggagtact gtcctccgag cggagtactg tcctccgagc ggagtactgt cctccgagca   1620
tcgcgtctca gcctcacttt aagcttcgcg aggcgaaact cgtaaatggt gccgatgctc   1680
tggaagagag ggatcaggcg gtcctcgtac acgtcgttcg ggatctgact gatgaaaacc   1740
tcacagcccg aaccaggagc aggaccctgc caacctggag gaggaccacc atatttcctc   1800
```

```
tgcccattga cttgggttaa agtgatggag ttcctctgca tccattcctg cagagacttg    1860
agtttctgcg ggttcagaat ctgctgaagc tcctgctgct gggcatccat gtctccgacc    1920
atctgtgatg atgatgatag acacacctgt aaattggtgg aaaagtcaag aaaaggtcat    1980
atctagataa ctgatcataa tcagccatac cacatttgta gaggttttac ttgctttaaa    2040
aaacctccca cacctccccc tgaacctgaa acataaaatg aatgcaattg ttgttgttaa    2100
cttgtttatt gcagcttata atggttacaa ataaagcaat agcatcacaa atttcacaaa    2160
taaagcattt ttttcactgc attctagttg tggtttgtcc aaacgcggcc gcc           2213
```